(12) United States Patent
Yanoff et al.

(10) Patent No.: US 7,065,177 B2
(45) Date of Patent: Jun. 20, 2006

(54) METHOD AND APPARATUS FOR CORRECTING A RETAINED IMAGE ARTIFACT

(75) Inventors: Brian David Yanoff, Schenectady, NY (US); Douglas Albagli, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 231 days.

(21) Appl. No.: 10/294,095

(22) Filed: Nov. 14, 2002

(65) Prior Publication Data

US 2004/0096036 A1    May 20, 2004

(51) Int. Cl.
*H05G 1/64* (2006.01)

(52) U.S. Cl. ................... 378/98.12; 378/98.8
(58) Field of Classification Search ............. 378/98.7, 378/98.8, 98.11, 98.12, 62; 250/370.08, 250/370.09, 370.11
See application file for complete search history.

(56) References Cited

U.S. PATENT DOCUMENTS

| | | | |
|---|---|---|---|
| 5,436,952 A * | 7/1995 | Haendle et al. ............. 378/98.7 |
| 5,452,338 A * | 9/1995 | Granfors et al. .......... 378/98.11 |
| 5,530,238 A * | 6/1996 | Meulenbrugge et al. .. 250/208.1 |
| 5,736,732 A | 4/1998 | Possin et al. ............. 250/208.1 |
| 5,923,722 A * | 7/1999 | Schulz ....................... 378/98.8 |
| 6,028,913 A * | 2/2000 | Meulenbrugge et al. ... 378/98.8 |
| 6,226,351 B1* | 5/2001 | Snoeren et al. .......... 378/98.12 |
| 6,243,441 B1* | 6/2001 | Zur ........................... 378/98.8 |
| 6,266,391 B1 | 7/2001 | Albagli ...................... 378/98.2 |
| 6,330,302 B1* | 12/2001 | Joosten .................... 378/98.12 |
| 6,343,112 B1* | 1/2002 | Petrick et al. ............. 378/98.9 |
| 6,351,519 B1* | 2/2002 | Bonk et al. ................ 378/98.8 |
| 6,393,098 B1 | 5/2002 | Albagli ...................... 378/98.2 |
| 6,453,008 B1* | 9/2002 | Sakaguchi et al. ......... 378/98.7 |
| 6,459,765 B1* | 10/2002 | Ganin et al. ................ 378/108 |
| 6,760,401 B1* | 7/2004 | Schmitz et al. ............... 378/62 |

* cited by examiner

*Primary Examiner*—Edward J. Glick
*Assistant Examiner*—Thomas R. Artman
(74) *Attorney, Agent, or Firm*—Fletcher Yoder

(57) ABSTRACT

A technique for compensating for a retained image includes employing bimodal readout of alternating light and dark images. The bimodal readout technique results from reading either light or dark frames more rapidly, allowing additional time to be allocated to the X-ray exposures occurring prior to the light frames or to the other reading operation. The bimodal readout may be accomplished by a binning procedure by which scan lines are binned and read, typically during dark frame readout. The images acquired from reading the dark frames may then be used to compensate for a retained image artifacts present in the image derived from light frames.

21 Claims, 5 Drawing Sheets

METHOD AND APPARATUS FOR CORRECTING A RETAINED IMAGE ARTIFACT

BACKGROUND OF THE INVENTION

The present invention relates generally to a technique for maintaining an effective X-ray dosage during imaging procedures. More particularly, the invention relates to increasing the X-ray dosage per image exposure while reducing the number exposure events such that an effective X-ray dosage is maintained during imaging.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector. The surface of the detector converts the radiation to light photons which are sensed. The detector is divided into a matrix of discrete picture elements or pixels, and encodes output signals based upon the quantity or intensity of the radiation impacting each pixel region. Because the radiation intensity is altered as the radiation passes through the patient, the images reconstructed based upon the output signals provide a projection of the patient's tissues similar to those available through conventional photographic film techniques.

Digital X-ray imaging systems are particularly useful due to their ability to collect digital data which can be reconstructed into the images required by radiologists and diagnosing physicians, and stored digitally or archived until needed. In conventional film-based radiography techniques, actual films were prepared, exposed, developed and stored for use by the radiologist. While the films provide an excellent diagnostic tool, particularly due to their ability to capture significant anatomical detail, they are inherently difficult to transmit between locations, such as from an imaging facility or department to various physician locations. The digital data produced by direct digital X-ray systems, on the other hand, can be processed and enhanced, stored, transmitted via networks, and used to reconstruct images which can be displayed on monitors and other soft copy displays at any desired location. Similar advantages are offered by digitizing systems which convert conventional radiographic images from film to digital data.

Despite their utility in capturing, storing and transmitting image data, digital X-ray systems are still overcoming a number of challenges. For example, X-ray systems may be employed for a range of different types of examination, including radiographic and fluoroscopic imaging. Among other distinctions, these two types of imaging examinations are characterized by significantly different radiation levels used to generate the image data. Specifically, radiographic imaging sequences employ substantially higher radiation levels than fluoroscopic imaging sequences. In a number of applications, it may be desirable to perform both types of imaging sequences sequentially to obtain different types of data and to subject patients to lower overall radiation levels. However, current digital X-ray systems may encounter difficulties in performing fluoroscopic imaging sequences following radiological sequences.

Specifically, current digital X-ray systems employ amorphous silicon detectors with arrays of photodiodes and thin film transistors beneath an X-ray scintillator. Incident X-rays interact with the scintillator to emit light photons which are absorbed by the photodiodes, creating electron-hole pairs. The diodes, which are initially charged with several volts of reverse bias, are thereby discharged in proportion to the intensity of the X-ray illumination. The thin film transistor switches associated with the diodes are then activated sequentially, and the diodes are recharged through charge sensitive circuitry, with the charge needed for this process being measured.

Raw signals from the detector may require several corrections to yield an accurate measure of the incident X-ray intensity. One of these corrections is for offset, or the signal which exists in the absence of X-ray illumination, which may result from current leakage in the diodes.

A second source for this residual signal is the previous history of illumination of the diodes, a phenomenon known as lag. Lag occurs when the signal strength associated with a pixel depends upon the preceding X-ray exposure event or events. Due to the nature of the amorphous silicon of the detector panel, the photodiodes contain traps which are filled after X-ray excitation, and which thereafter empty in a decay process with a relatively long time constant. As a result, a decaying image is retained by the detector. The magnitude of image retention in X-ray detectors is relatively small, and decays with time as the traps empty thermally so that the lag signal will slowly decay away until it is no longer visible. In single-shot radiographic applications, image retention does not generally cause problems because a relatively long period of time exists between exposures.

Image retention in X-ray detectors poses a substantial problem, however, in applications requiring mixed radiographic and fluoroscopic operation. Again, because the fluoroscopic signal levels are substantially lower (e.g. two to three orders of magnitude smaller) than the radiographic signals, when a fluoroscopic imaging sequence follows a radiographic exposure, the retained image, although a small fraction of the radiographic signal, can be comparable to or even larger than the fluoroscopic signal. If uncorrected, a ghost of the radiographic image will appear in the reconstructed fluoroscopic image.

One technique which is employed to reduce the effects of lag in mixed radiographic and fluoroscopic operation is to operate the X-ray tube at half the frame rate of the X-ray detector during fluoroscopy. Because of this differential between the operation of the X-ray tube and the detector, every alternate reading of the detector occurs in the absence of an X-ray exposure and therefore provides a measure of lag at that acquisition time. The measures of lag determined from these dark frames can then be used to correct the light frames either in real-time or offline.

However to maintain the same image quality while employing this lag correction technique, approximately the same dose of X-rays per second must be delivered to the detector with half the number of exposures. To accomplish this dosage requirement, either the X-ray flux per exposure or the duration of the exposure is doubled or an equivalent combination of increased flux and duration is employed. In some operating conditions, such as thick patients, the maximum duration may already be employed, however. Likewise increasing the peak X-ray flux per exposure can stress the X-ray tube and thereby degrade the tube lifetime.

There is a need, therefore, for an improved technique for maintaining image quality while allowing for lag correction during mixed radiographic and fluoroscopic operations. There is a particular need for a technique which can increase the available exposure time during fluoroscopic imaging such that the same X-ray dose per second can be delivered to the detector at a reduced number of exposures without degrading X-ray tube performance.

BRIEF DESCRIPTION OF THE INVENTION

The present invention provides a technique designed to allow the duration of an X-ray exposure to be increased by reducing the time required to perform alternating readout operations. The technique is particularly well suited to fluoroscopic imaging where lag correction is performed, such as after a radiographic exposure. In such circumstances, the readout operation performed on dark frames, to obtain a lag correction image, may be performed more quickly than the readout operation performed on light frames, resulting in a bimodal readout operation. Bimodal readout performed in this manner allows additional time to be spent on fluoroscopic exposure intervals. However, the technique may be advantageously employed in other domains, including within and outside the medical diagnostic imaging field, where appropriate. Moreover, the present technique may be employed in both existing systems, as well as in new or future digital imaging systems, particularly those employing amorphous silicon detectors. Because the technique is based upon sampling of data from the detector, and processing the sampled data in accordance with a computer-implemented routine, it is susceptible to use in imaging systems both in their basic control algorithms, as well as in patches or enhancements to existing control or signal processing software.

In accordance with one aspect of the present technique, a method for compensating for image retention in a digital imaging system is provided. The method includes steps of acquiring two or more dark frames of a first duration following a primary exposure event, wherein each dark frame is followed by a secondary exposure event. In addition, the step of acquiring a light frame of a second duration after each secondary exposure event is included. Further, the steps of calculating a lag correction image for each light frame using at least one preceding dark frame and correcting an image derived from the light frame with the lag correction image are also included.

In accordance with a further aspect of the present technique, a medical imaging system is provided comprising a source of a radiation stream and a detector configured to detect a portion of the radiation stream. In addition the system includes a system controller operably coupled to the source and a detector controller operably coupled to the system controller and the detector. At least one of the system controller and the detector controller are configured to acquire two or more dark frames of a first duration following a primary exposure event, wherein each dark frame is followed by a secondary exposure event. At least one of the system controller and the detector controller are also configured to acquire a light frame of a second duration after each secondary exposure event, to calculate a lag correction image for each light frame using at least one preceding dark frame, and to correct an image derived from the light frame with the lag correction image.

In accordance with a further aspect of the present technique, a method is provided for acquiring an unexposed frame of an X-ray imaging sequence. The method comprises the steps of activating two or more scan lines of the detector simultaneously and draining two or more photodiodes distributed on the two or more activated scan lines by one or more respective channels. These steps are repeated incrementally until all scan lines of a detector have been activated.

In accordance with another aspect of the present technique, an X-ray imaging system is provided comprising an X-ray source and a detector configured to detect X-rays. In addition, the system includes a system controller operably coupled to the source and a detector controller operably coupled to the system controller and the detector. At least one of the system controller and the detector controller are configured acquire an unexposed X-ray image by sequentially activating two or more scan lines simultaneously and draining two or more photodiodes distributed on the two or more activated scan lines by one or more respective channels. At least one of the system controller and the detector controller are further configured to proceed to the next two or more scan lines until all of the scan lines of the detector have been activated.

In accordance with a further aspect of the present technique, a computer program for correction of image data in a digital X-ray imaging system is provided. The computer program comprises a machine readable medium for storing programming code and programming code stored on the machine readable medium. The programming code provides instructions for at least one of a system controller and a detector controller of an imaging system for acquiring two or more dark frames of a first duration following a primary exposure event, wherein each dark frame is followed by a secondary exposure event. The programming code also provides instructions for acquiring a light frame of a second duration after each secondary exposure event, for calculating a lag correction image for each light frame using at least one preceding dark frame, and for correcting an image derived from the light frame with the lag correction image.

In accordance with another aspect of the present technique, a medical imaging system is provided comprising a source of a radiation stream and a detector configured to detect a portion of the radiation stream. The system also includes a system controller operably coupled to the source and a detector controller operably coupled to the system controller and the detector. At least one of the system controller and the detector controller comprise a means for implementing a bimodal readout of alternating dark frames and light frames. At least one of the system controller and the detector controller also include a means for calculating a lag correction image for each light frame wherein an image derived from the light frame is corrected by the respective lag correction image.

DETAILED DESCRIPTION OF SPECIFIC EMBODIMENTS

Figure 1:
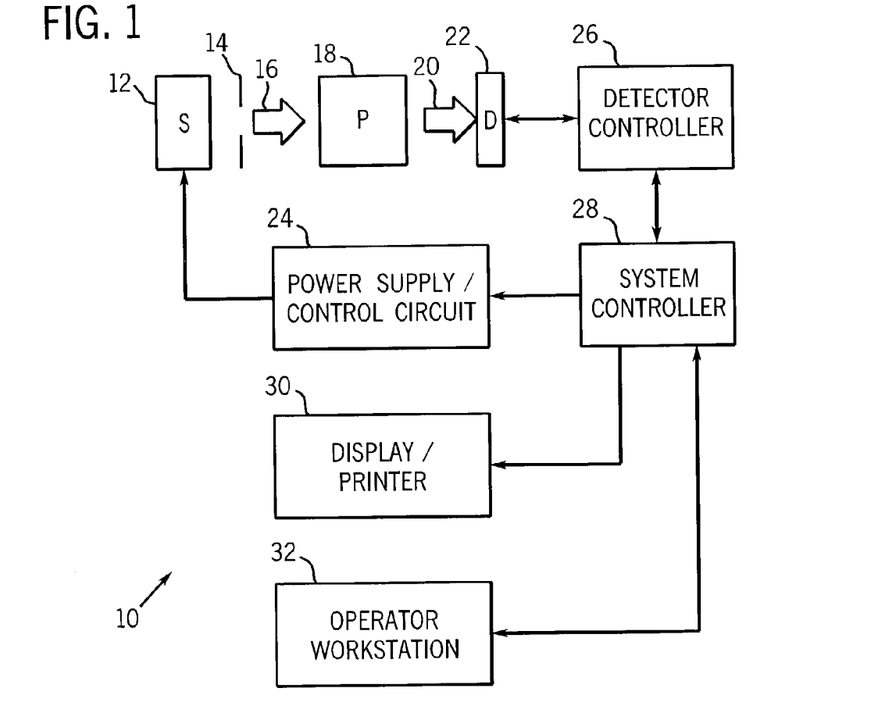
FIG. 1 is a diagrammatical overview of a digital X-ray imaging system in which the present technique is incorporated.

FIG. 1 illustrates diagrammatically an imaging system 10 for acquiring and processing discrete pixel image data. In the illustrated embodiment, system 10 is a digital X-ray system designed both to acquire original image data, and to process the image data for display in accordance with the present technique. Throughout the following discussion, however, while basic and background information is provided on the digital X-ray system, it should be borne in mind that aspects of the present technique may be applied to other types of systems for compensating for decaying retained images.

In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28.

In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked to the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
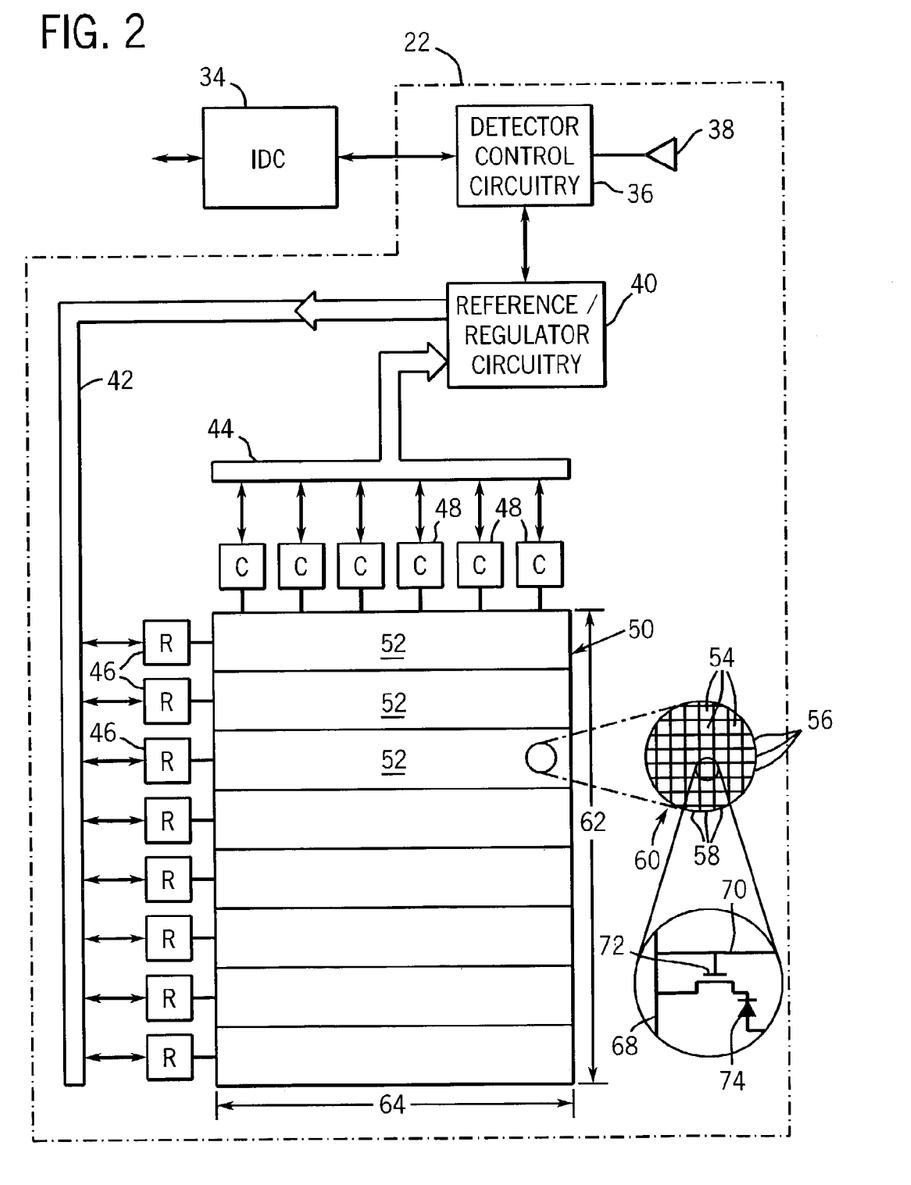
FIG. 2 is a diagrammatical representation of certain of the functional circuitry for producing image data in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In a present embodiment illustrated, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions of the detector surface. As described below, readout electronics convert the resulting analog signals to digital values that can be processed, stored, and displayed, such as in a display 30 or a workstation 32 following reconstruction of the image. In a presently preferred embodiment, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics described below. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
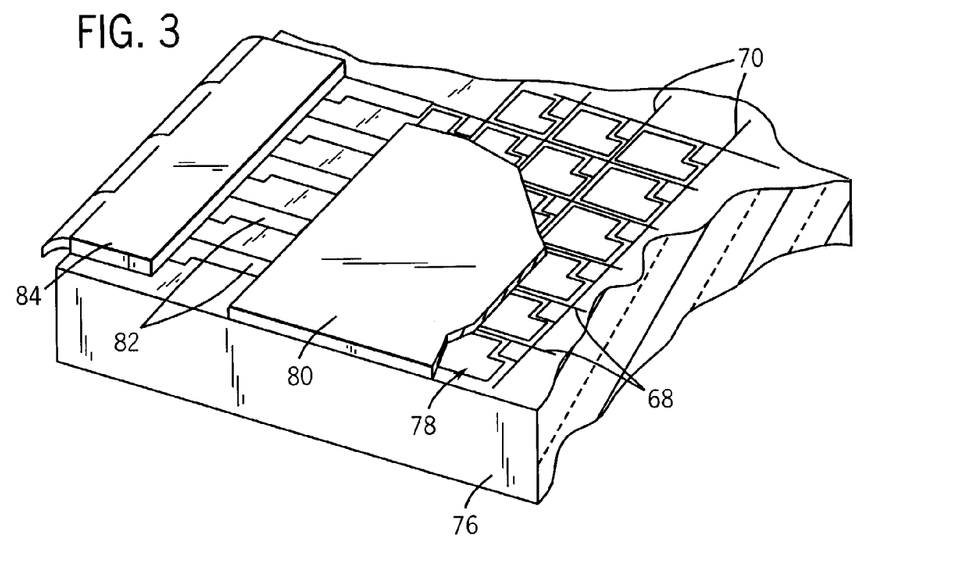
FIG. 3 is a partial sectional view illustrating an exemplary detector structure for producing the image data.

FIG. 3 generally represents an exemplary physical arrangement of the components illustrated diagramatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry.

It has been found that in systems employing the foregoing structure, photodiodes 74 contain traps which are filled after X-ray excitation, and which thereafter empty with relatively long time constants. As a result, in higher exposure imaging sequences, an image may be retained by the detector which decays over time as the traps empty. While in certain imaging sequences this image retention may not pose difficulties, it may be particularly problematic where relatively low intensity radiation is employed following higher radiation level exposures. This is particularly the case where fluoroscopic exposures are performed in relatively short delays after radiographic exposures.

Figure 4:
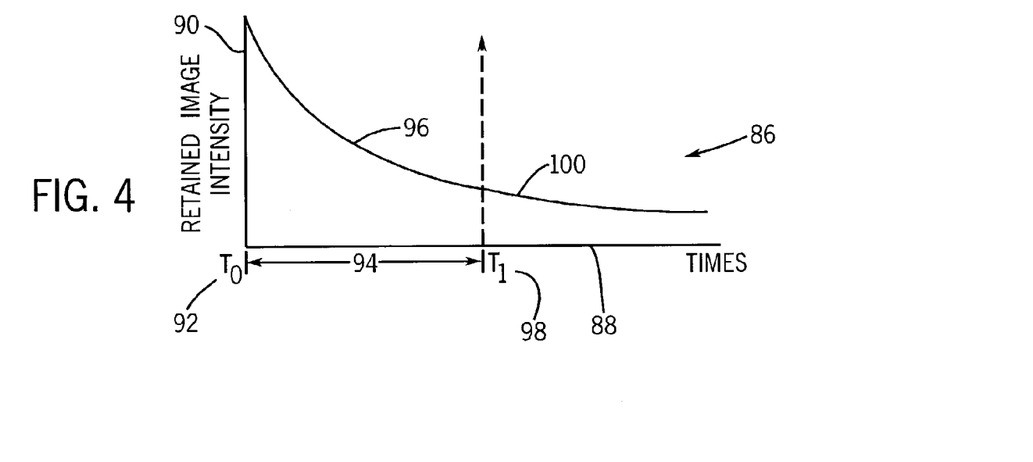
FIG. 4 is a graphical representation of a decaying retained image function.

The decay function 86 of a retained image following an exposure of the detector 22 to radiation is graphically illustrated in FIG. 4. In FIG. 4, time is represented along a horizontal axis 88, with the retained image intensity being indicated generally by a vertical axis 90. As will be appreciated by those skilled in the art, in practice, the particular portion of the image retained at each pixel region may differ over the dynamic range of the detector, such that an entire retained image is defined by the image matrix, the portion of the image defined at each pixel region decaying from its initial value.

In the graphical illustration of FIG. 4, a radiographic exposure (or more generally a first imaging sequence or examination) ends at an initial time $t_0$ as indicated at reference numeral 92. During an interim period 94, the intensity or level of the retained image decays as indicated at reference numeral 96. Interim period 94 is generally defined as the period between the end of the previous exposure and the beginning of a subsequent exposure, a fluoroscopic image exposure in the example of FIG. 4. The subsequent exposure begins at time $t_1$, as indicated at reference numeral 98, marking the end of the interim period 94. However, because the retained image has not yet decayed to a null value, decay continues as indicated at reference numeral 100.

Figure 5:
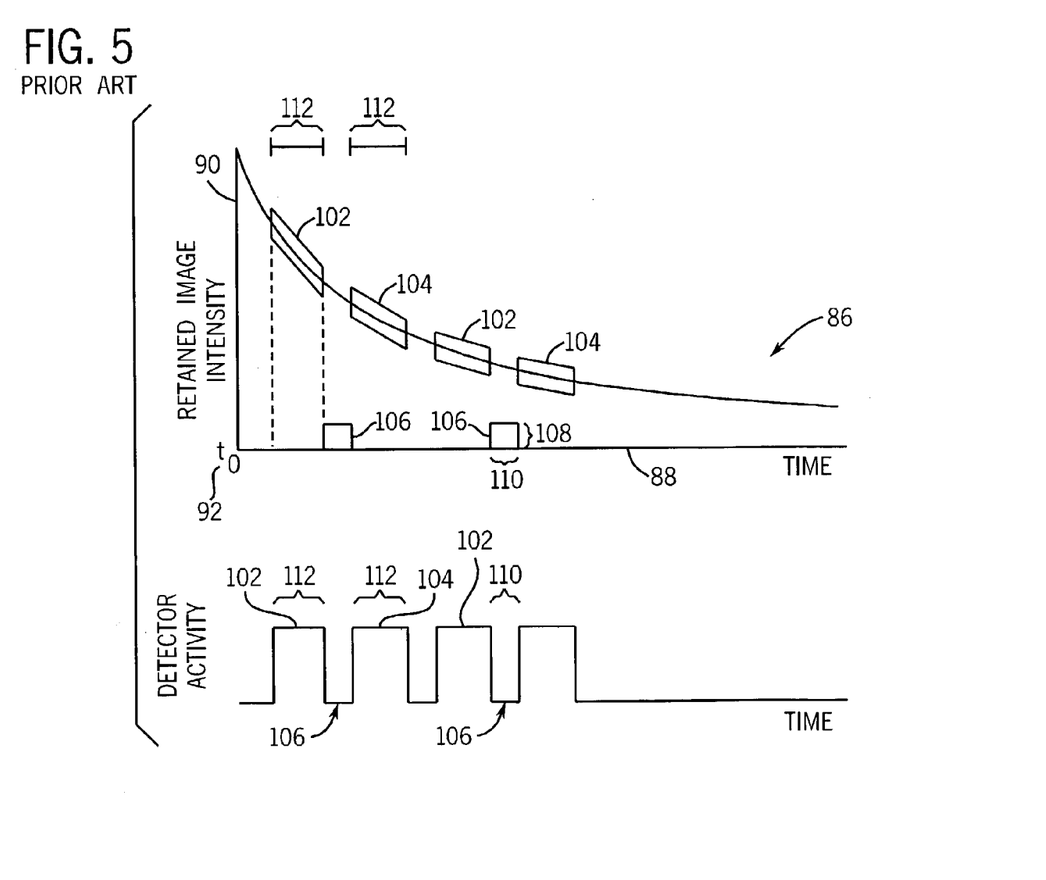
FIG. 5 is a graphical representation of a decaying retained image function illustrating the prior technique for reading light and dark frames during fluoroscopy.

In the case of a fluoroscopic exposure following a radiographic exposure, and where interim period 94 is relatively short, the retained image, although decaying, may be comparable in pixel signal levels, or even larger than the levels produced during the subsequent exposure. To compensate for this retained image, the detector 22 may be operated at frame rate, F, while the X-ray tube in the source 12 operates at half the frame rate, F/2, as depicted in FIG. 5. The frame rate differential between the detector 22 and the source 12 results in alternating unexposed or "dark" frames 102 being read by the detector 12 which provide a measure of the lag, or image retention, in that frame. The measure of lag provided by the dark frames can then be used to remove the retained image from the alternating exposed or "light" frames 104 which are acquired subsequent to a fluoroscopic X-ray exposure 106. Typically, a "lag image" is calculated and subtracted from the "light image" subsequent to subtraction of any necessary offset image.

This technique is useful in correcting for the retained image but presents other image quality problems. In particular, the same X-ray dose per second is delivered to the detector 22 in half the number of fluoroscopic exposures 106. To accomplish this, the X-ray flux 108 per exposure 106 is doubled, the exposure time 110 is doubled, or some equivalent combination of increased flux 108 and exposure duration 110 is accomplished. In many circumstances, such as for thick patients, the exposure duration 110 is already maximized, allowing for no further increase. Likewise, in some circumstances, such as cardiac imaging, the fluoroscopic flux 108 may already be maximized. However, even when fluoroscopic flux 108 is not already maximized, increasing the peak output per exposure 106 appreciably degrades X-ray tube lifetime.

Figure 6:
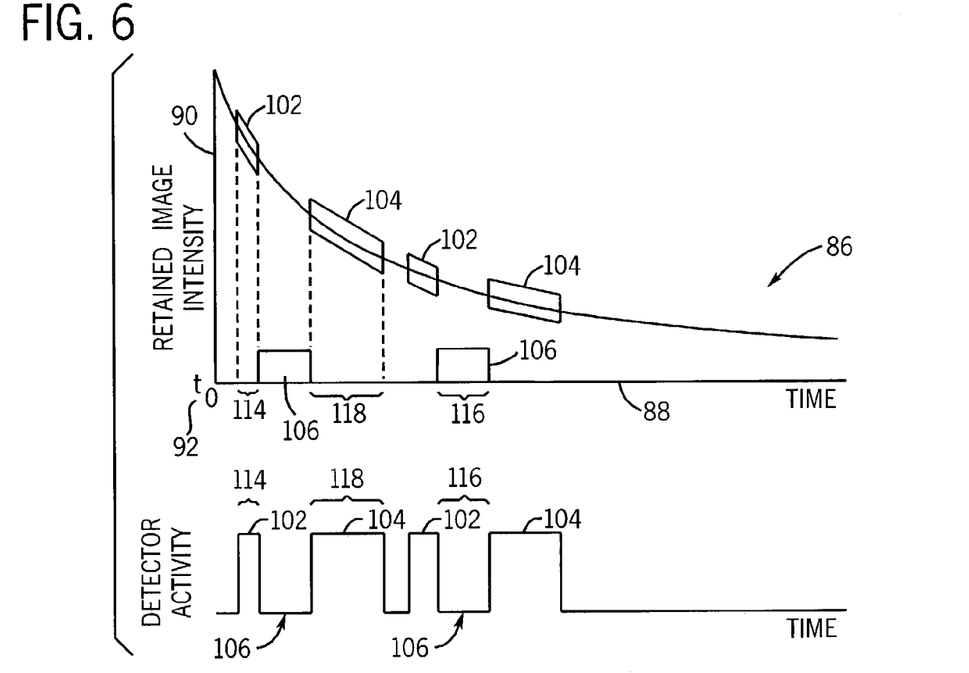
FIG. 6 is a graphical representation of a decaying retained image function illustrating the present technique for reading light and dark frames during fluoroscopy.

One factor which constrains the extent to which the exposure duration 110 can be increased is the readout duration 112 required to readout the respective dark and light frames 102, 104 by the detector 22, as depicted in an associated detector timeline in FIG. 5. One technique by which the exposure duration 110 may be increased is to employ a bimodal readout operation with the dark and light frame readout durations alternating between two values. For instance, the readout duration 112 for either the dark or light frames may be shortened, thereby easing the exposure time constraints imposed by the detector 22 and allowing the exposure duration 110 to be correspondingly increased. This may be accomplished by reading one frame type, typically the dark frames 102, faster than the other frame type. This technique is depicted in FIG. 6, in which a reduced readout duration 114 is employed for reading dark frames 102. Due to the reduction in the dark readout duration 114, an extended exposure duration 116 can be employed which allows the same dose per second to be delivered to the detector 22 without degrading the X-ray tube. In addition, the time made available by using a shortened dark readout duration 114 can be used to perform real-time image processing, such as the processing required to calculate the lag correction.

Similarly, due to the use of a reduced dark readout duration 114, an extended light readout duration 118 may be employed to allow a reduction in bandwidth, thereby reducing noise. In addition, an extended light readout duration 118 can increase the number of analog-to-digital conversion steps, which can reduce quantization errors or increase dynamic range. Likewise, an extended light readout duration 118 can allow an increase in FET on time, reducing offset dispersion.

However, the bimodal readout technique introduces some complexity not present in single mode readout techniques. For example, because frame readout duration strongly influences baseline offset of the detector 22, a separate frame offset image is maintained for the light and dark frames, respectively, using a bimodal readout technique. In addition, the bimodal readout introduces a row-dependent frame time, which is captured in the offset image. This may imply different analog-to-digital conversion processes for the light and dark frames. Further, the calculation of the lag correction is modified by the use of bimodal readout.

Lag prediction using single mode readout techniques is made using the equation:

$$\log \tilde{L}(n) = \log L_D(n-1) - x(\log(n) - \log(n-1)), \quad (1)$$

in which $\tilde{L}(n)$ is the predicted lag in light frame n, $L_D(n-1)$ is the retained image reading of dark frame n−1 immediately preceding light frame n, and −x is the slope on a log-log plot given by:

$$-x = \frac{\log L_D(n-1) - \log L_D(n-3)}{\log(n-1) - \log(n-3)}, \quad (2)$$

where frame n−3 is the dark frame preceding frame n−1, i.e. frames n−1 and n−3 are the two dark frames preceding light frame n.

As noted above, when bimodal timing is used, frame time is different for dark and light frames and is typically row number-dependent. This row number dependence can be expressed in terms of the frame time of the first row such that:

$$T_{F(Light)}(i) = T_{F(Light)}(1) - (T_L - T_D) \cdot (i/i_{max}), \text{ and} \quad (3a)$$

$$T_{F(Dark)}(i) = T_{F(Dark)}(1) + (T_L - T_D) \cdot (i/i_{max}), \quad (3b)$$

where $T_{F(Light)}$ and $T_{F(Dark)}$ are the frame times of the light and dark frames respectively, i is the row number, $i_{max}$ is the last row of the panel, and $T_L$ and $T_D$ are the duration of the light and dark frame readout respectively. The predicted lag in the light frame is then determined by the ratio:

$$\frac{L_L(n)}{L_D(n-1)} \approx \frac{T_{F(Dark)}(i)}{T_{F(Light)}(i)} \cdot \left(\frac{n-1}{n}\right)^x \left[1 - \frac{x}{n}\left(\frac{T_F - 2D}{T_F}\right)\left(\frac{\Delta t}{T_F}\right)\right], \quad (4)$$

where terms up to first order in 1/n have been retained in the last factor, and D may be been neglected relative to $nT_F$. Keeping only the leading term and taking the log of both sides, the log-log prediction equation using a bimodal readout technique is given by the equation:

$$\log \tilde{L}_L(n) = \log L_D(n-1) - x(\log(n) - \log(n-1)) + \log\left(\frac{T_{F(Dark)}(i)}{T_{F(Light)}(i)}\right), \quad (5)$$

where the value of x is based upon the two most recent dark readings, n−1 and n−3 as given by equation (2). The last term on the right-hand side of equation (5) accounts for the difference in frame timing and is dependent upon row number. This is equivalent to approximating the ratio in equation (4) as:

$$\frac{L_L(n)}{L_D(n-1)} \approx \frac{T_{F(Dark)}(i)}{T_{F(Light)}(i)} \cdot \left(\frac{n-1}{n}\right)^x. \quad (6)$$

Higher order terms can be retained in the log-log prediction formula if desired.

One technique by which a bimodal readout technique may be implemented is to employ pixel binning to read the dark frames 102 in a shorter time, thereby making time available for an extended exposure time 116, an extended light frame 104, or both. For example, using a binned readout, two or more adjacent scan lines 70 are activated simultaneously. The charge from multiple pixels will drain onto each scan line 70 simultaneously and enter a single input channel 68 of the readout electronics. In this manner, the two analog signals are added before analog-to-digital conversion. The number of scan lines activated simultaneously is inversely proportional to the reduction in readout time for that frame, i.e. by reading M rows at a time, the total readout time of the detector is reduced to approximately 1/M with some overhead associated with the beginning and end of the panel scan.

Figure 7:
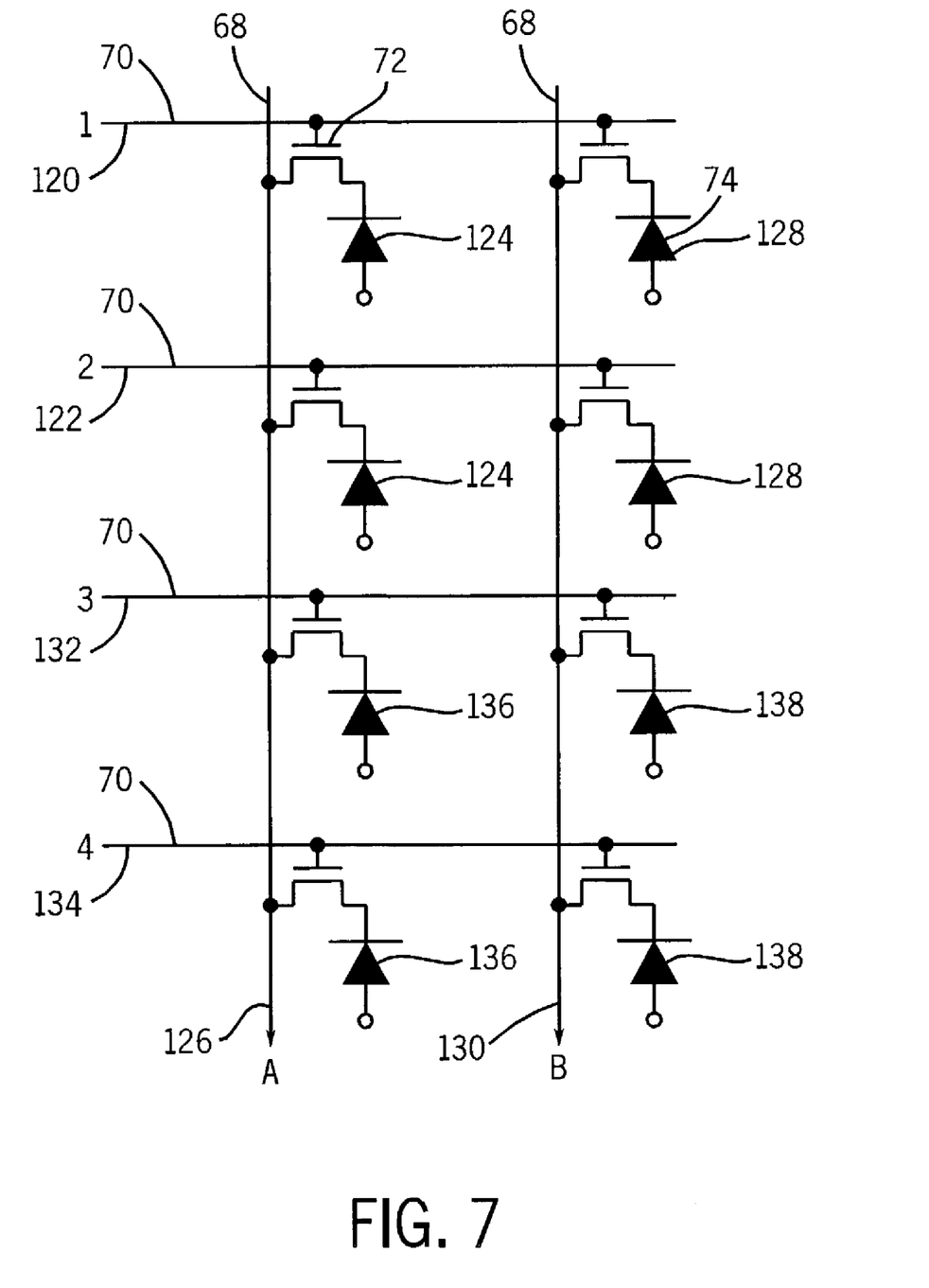
FIG. 7 is a partial electrical circuit depicting scan and channel lines accessed by readout circuitry in an X-ray imaging system.

For example, referring to the partial array depicted in FIG. 7, the first scan line 120 and second scan line 122 are activated simultaneously, allowing the photodiodes of a first color 124 to drain onto channel A 126 and the photodiodes of a second color 128 to drain onto channel B 130. Next, the third scan line 132 and fourth scan line 134 are activated simultaneously, draining the photodiodes of a third color 136 onto channel A 126 and the photodiodes of a fourth color 138 onto channel B 130. By reading scan lines 70 in pairs in this manner, the readout time 114 is approximately reduced to half. Though the dark frames are read in a binned manner, the light frames are read normally, i.e. one row at a time, producing the bimodal readout times.

Using a binned readout of the dark frame, the pixel signals are combined as analog signals prior to analog-to-digital conversion during the binning process. By combining the analog signals, the relative level of electronic noise that accompanies the readout is reduced compared to reading the pixels individually and combining the results digitally. In addition, some spatial averaging of the dark offset image is accomplished automatically by the binning procedure, which is beneficial for reducing the noise in the lag-corrected images. While these added benefits may accrue from employing pixel binning for dark image readout, some detriments may also occur.

For example, because bad pixels (i.e. pixel regions of which the associated electronic circuitry produces aberrant or statistically excessively high or low signals) may be binned together with good pixels, algorithms for locating and correcting bad pixels can be modified as necessary during the binning process, such as by marking both pixels as bad when a good pixel is binned with a bad one. In addition, using a binning technique to reduce the dark frame readout time results in dark and light images of different resolutions, i.e. a high-resolution light image and a low-resolution dark image. As the final stage of lag correction, the lag prediction image derived from binned data must be upscanned back to a high-resolution prior to subtraction from the high-resolution light frame to make the image spatial resolution comparable.

By use of these pixel binning techniques or other comparable techniques by which bimodal detector readout can be accomplished, the timing benefits discussed above can be achieved. In particular, referring once again to FIGS. 5 and 6, the shortening of either the dark or light frame readout 112 allows a corresponding increase in the fluoroscopic exposure time 116 with associated benefits allowing a uniform dose per second to be delivered by the X-ray tube without degrading the tube life. In the depicted example, the dark frame readout duration 114 is shortened, allowing not only the increase in the fluoroscopic exposure time 116 but also an increase in the light frame readout duration 118 which reduces image noise as well as providing other benefits.

While the use of bimodal readout times, whether by binned readout or otherwise, yield the benefits discussed above in the medical imaging context, it should be understood that other imaging technologies which rely upon lag images or other subtractive image acquisitions may benefit from the bimodal benefits discussed. While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for compensating for image retention in a digital imaging system, the method comprising the steps of:
   acquiring two or more dark frames of a first duration following a primary exposure event, wherein each dark frame is followed by a secondary exposure event;
   acquiring a light frame of a second duration after each secondary exposure event;
   calculating a lag correction image for each light frame using at least one preceding dark frame;
   correcting a respective image with the lag correction image; and
   adjusting the resolution of the lag correction image to the resolution of the respective image prior to the act of correcting.

2. The method as recited in claim 1, wherein the first duration is less than the second duration.

3. The method as recited in claim 1, wherein the primary exposure event is a radiographic exposure event and the secondary exposure event is a fluoroscopic exposure event.

4. The method as recited in claim 1, wherein calculating the lag correction image comprises using two preceding dark frames.

5. The method as recited in claim 1, wherein correcting the light frame comprises subtracting the lag correction image from the image derived from the light frame.

6. A medical imaging system, comprising:
   a source of a radiation stream;
   a detector configured to detect a portion of the radiation stream;
   a system controller operably coupled to the source; and
   a detector controller operably coupled to the system controller and the detector;
   wherein at least one of the system controller and the detector controller are configured to acquire two or more dark frames of a first duration following a primary exposure event, wherein each dark frame is followed by a secondary exposure event, to acquire a light frame of a second duration after each secondary exposure event, to calculate a lag correction image for each light frame using at least one preceding dark frame, and to correct a respective image with the lag correction image, wherein the at least one of the system controller and the detector controller is further configured to adjust the resolution of the lag correction image to the resolution of the respective image prior to the act of correcting.

7. The medical imaging system as recited in claim 6, further comprising a display device operably coupled to the system controller.

8. The medical imaging system as recited in claim 6, further comprising an operator workstation operably coupled to the system controller.

9. The medical imaging system as recited in claim 6, wherein the source is a source of X-rays.

10. The medical imaging system as recited in claim 9, wherein the detector is a digital detector.

11. The medical imaging system as recited in claim 10, wherein the primary exposure event is a radiographic exposure event and the secondary exposure event is a fluoroscopic exposure event.

12. The medical imaging system as recited in claim 6, wherein first duration is less than the second duration.

13. The medical imaging system as recited in claim 6, wherein the lag correction image is calculated using two preceding dark frames.

14. The medical imaging system as recited in claim 6, wherein the at least one of the system controller and the detector controller is configured to correct the light frame by subtracting the lag correction image from the image derived from the light frame.

15. A computer-readable medium, comprising:
   a routine for acquiring two or more dark frames of a first duration following a primary exposure event, wherein each dark frame is followed by a secondary exposure event;
   a routine for acquiring a light frame of a second duration after each secondary exposure event;
   a routine for calculating a lag correction image for each light frame using at least one preceding dark frame;
   a routine for correcting a respective image with the lag correction image; and
   a routine for adjusting the resolution of the lag correction image to the resolution of the respective image.

16. The computer-readable medium as recited in claim 15, wherein the first duration is less than the second duration.

17. The computer-readable medium as recited in claim 15, wherein the routine for calculating the lag correction image calculates the lag correction image using two preceding dark frames.

18. The computer-readable medium as recited in claim 15, wherein the routine for correcting the image corrects the light frame by subtracting the lag correction image from the image derived from the light frame.

19. The computer-readable medium of claim 15, wherein the computer-readable medium is a component of an image processing system.

20. The computer-readable medium of claim 15, wherein at least one routine is transferred to the computer-readable medium via a configurable network connection.

21. A medical imaging system, comprising:
   a source of a radiation stream;
   a detector configured to detect a portion of the radiation stream;
   a system controller operably coupled to the source; and
   a detector controller operably coupled to the system controller and the detector;
   wherein at least one of the system controller and the detector controller comprise a means for implementing a readout of alternating dark frames and light frames in which the readout of the respective dark frames and light frames occur at different speeds and a means for calculating a lag correction image for each light frame wherein an image derived from the light frame is corrected by the respective lag correction image.

* * * * *